United States Patent [19]
Cotteret et al.

[11] Patent Number: 5,580,357
[45] Date of Patent: Dec. 3, 1996

[54] COMPOSITION FOR THE OXIDATION DYEING OF KERATINOUS FIBRES COMPRISING A PARA-AMINOPHENOL, A META-AMINOPHENOL AND AN ORTHO-AMINOPHENOL, AND DYEING PROCESS USING SUCH A COMPOSITION

[75] Inventors: Jean Cotteret, Verneuil-sur-Seine; Marie P. Audousset, Asnières; Alain Lagrange, Coupvray; Jean J. Vandenbosche, Sevran, all of France

[73] Assignee: L'Oreal, Paris, France

[21] Appl. No.: 379,524

[22] PCT Filed: Jun. 14, 1994

[86] PCT No.: PCT/FR94/00709

§ 371 Date: Apr. 6, 1995

§ 102(e) Date: Apr. 6, 1995

[87] PCT Pub. No.: WO94/28864

PCT Pub. Date: Dec. 22, 1994

[30] Foreign Application Priority Data

Jun. 16, 1993 [FR] France .................. 93 07238

[51] Int. Cl.$^6$ .................................................. A61K 7/13
[52] U.S. Cl. .................. 8/408; 8/406; 8/407; 8/409; 8/421
[58] Field of Search ....................... 8/405, 406, 407, 8/408, 409, 412, 421

[56] References Cited

U.S. PATENT DOCUMENTS

| | | | |
|---|---|---|---|
| 4,065,255 | 12/1977 | Andrillon et al. | 8/412 |
| 4,268,264 | 5/1981 | Grollier et al. | 8/412 |
| 4,295,848 | 10/1981 | Grollier et al. | 8/421 |
| 4,323,360 | 4/1982 | Bugaut et al. | 8/408 |
| 4,324,553 | 4/1982 | Bugaut et al. | 8/421 |
| 4,333,730 | 6/1982 | Bugaut et al. | 8/421 |
| 4,883,656 | 11/1989 | Konrad et al. | 8/412 |
| 5,145,483 | 9/1992 | Junino et al. | 8/421 |

FOREIGN PATENT DOCUMENTS

| | | |
|---|---|---|
| 625116 | 11/1962 | Belgium . |
| 0366542 | 5/1990 | European Pat. Off. . |
| 0459901 | 12/1991 | European Pat. Off. . |
| 2421869 | 12/1979 | France . |
| 2421870 | 12/1979 | France . |
| 2018808 | 10/1979 | United Kingdom . |
| 2054663 | 2/1981 | United Kingdom . |
| 86/02829 | 5/1986 | WIPO . |
| 9300066 | 1/1993 | WIPO . |

*Primary Examiner*—Paul Lieberman
*Assistant Examiner*—Caroline L. Dusheck
*Attorney, Agent, or Firm*—Jacobson, Price, Holman & Stern, PLLC

[57] ABSTRACT

A dyeing composition for keratinous fibers and in particular for human keratinous fibers such as hair, comprising, in a suitable dyeing medium, at least one oxidation dye precursor chosen from 3-methyl-para-aminophenol, 2-methyl-para-aminophenol and 2-hydroxymethyl-para-aminophenol and their addition salts with an acid; at least one coupling agent chosen from the 2-methyl-5-aminophenols of formula (I):

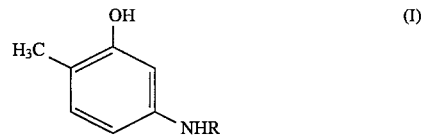

where R denotes hydrogen, methyl, ethyl, β-hydroxyethyl or γ-hydroxypropyl, and their addition salts with an acid; and at least one ortho-aminophenol chosen from ortho-aminophenol and 3-acetylamino-6-aminophenol or one of their addition salts with an acid. A dyeing process incorporates development by an oxidizing agent.

23 Claims, No Drawings

COMPOSITION FOR THE OXIDATION DYEING OF KERATINOUS FIBRES COMPRISING A PARA-AMINOPHENOL, A META-AMINOPHENOL AND AN ORTHO-AMINOPHENOL, AND DYEING PROCESS USING SUCH A COMPOSITION

The present invention relates to a composition for the dyeing of keratinous fibres, and in particular of human keratinous fibres, comprising, in combination, at least one para-aminophenol, at least one 2-substituted 5-aminophenol and at least one ortho-aminophenol, and to the dyeing process using such a composition and incorporating development with an oxidizing agent.

It is known to dye keratinous fibres, and in particular human hair, with dyeing compositions which contain oxidation dye precursors, in particular ortho- or para-phenylenediamines, ortho- or para-aminophenols, generally known as "oxidation bases", and coupling agents also known as coloration modifiers, more particularly aromatic meta-phenylenediamines, meta-aminophenols and meta-diphenols, which make it possible to modify and to enrich with glints the "foundation" colours obtained by the condensation products of the oxidation bases.

In the field of the oxidation dyeing of hair, oxidation dye precursors and coupling agents are sought which make it possible to impart to the hair a coloration which has a satisfactory resistance to light, to washing, to inclement weather, to perspiration and to the various treatments to which hair may be subjected, and which make it possible to obtain a wide range of colour shades.

3-Methyl-para-aminophenol and its use in dyeing compositions for keratinous fibres, in combination with 2-methyl-5-aminophenol as coupling agent and para-phenylenedisunine or 2,5-diaminotoluene, are known and described in U.S. Pat. No. 4,883,656.

However, such a combination, on application to keratinous fibres, does not provide a sufficiently resistant coloration.

The Applicant has just discovered, and this forms the subject of the invention, that the use of 3-methyl-para-aminophenol, 2-methyl-para-aminophenol and/or 2-hydroxymethyl-para-aminophenol as oxidation dye precursors, in combination with, as coupling agent, a 5-aminophenol substituted in the 2-position chosen from the 2-methyl-5-aminophenols of formula (I) defined below and, as oxidation dye precursor, an ortho-aminophenol chosen from ortho-aminophenol and 3-acetylamino-6-aminophenol, makes it possible to obtain, in the presence of an oxidizing agent and in an acidic or alkaline medium, after application to keratinous fibres and in particular to human hair, colorations with warm and coppery shades and having a resistance to light, to washing, to inclement weather, to perspiration and to the various treatments to which hair may be subjected, and which is particularly noteworthy and superior to that of the prior art.

The subject of the present invention is thus a composition for the dyeing of keratinous fibres, in particular human keratinous fibres such as hair, comprising, in a suitable dyeing medium:

at least one oxidation dye precursor chosen from 3-methyl-para-aminophenol, 2-methyl-para-aminophenol and 2-hydroxymethyl-para-aminophenol and their addition salts with an acid;

at least one coupling agent chosen from the 2-methyl-5-aminophenols of formula (I) below:

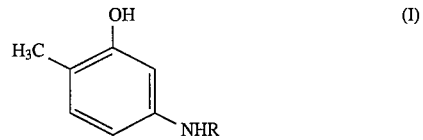

in which R denotes a hydrogen atom, a methyl or ethyl radical or a β-hydroxyethyl or γ-hydroxypropyl group, as well as their addition salts with an acid; and at least one ortho-aminophenol, as oxidation dye precursor, chosen from ortho-aminophenol and 3-acetylamino-6-aminophenol, or one of their addition salts with an acid.

The subject of the invention is also a dyeing agent containing several components, of which the first component contains oxidation dye precursors and the coupling agent defined above and the second component contains an oxidizing agent.

Another subject of the invention relates to the ready-to-use composition, containing the various agents used for dyeing keratinous fibres defined above and an oxidizing agent, in an alkaline or acidic medium.

The invention also concerns a process for the dyeing of keratinous fibres, and in particular human keratinous fibres such as hair, which consists in applying to these fibres:

at least one oxidation dye precursor chosen from 3-methyl-para-aminophenol, 2-methyl-para-aminophenol and 2-hydroxymethyl-para-aminophenol and their addition salts with an acid;

at least one coupling agent chosen from 2-methyl-5-aminophenols of formula (I) above, as well as their addition salts with an acid;

at least one ortho-aminophenol, as oxidation dye precursor, chosen from ortho-aminophenol and 3-acetylamino-6-aminophenol or one of their addition salts with an acid;

the colour being developed at acidic or alkaline pH using an oxidizing agent.

According to the invention and among the precursors of para type above, 3-methyl-p-aminophenol is preferred.

Among the coupling agents mentioned above, 2-methyl-5-aminophenol is preferred for use according to the invention.

According to the process in accordance with the invention, there is applied to human keratinous fibres at least one composition (A) containing, in a suitable dyeing medium:

at least one oxidation dye precursor chosen from 3-methyl-para-aminophenol, 2-methyl-para-aminophenol, 2-hydroxymethyl-para-aminophenol and their salts;

at least one coupling agent chosen from the 2-methyl-5-aminophenols of formula (I) above, and their salts;

at least one ortho-aminophenol chosen from ortho-aminophenol and 3-acetylamino-6-aminophenol, or one of their salts;

the colour being developed in an acidic or alkaline medium using an oxidizing agent which is added just at the time of use to the composition (A) or which is present in a composition (B) which is applied simultaneously or sequentially in a distinct manner.

The subject of the invention is also dyeing devices or "kits", containing several compartments, making it possible to implement the process indicated above.

Such a dyeing kit contains at least two compartments, the first of which contains the composition (A) as defined above and the second contains the composition (B) comprising an oxidizing agent in a suitable dyeing medium.

Other subjects of the invention will emerge on reading the description and the examples which follow.

The acid salts used according to the invention are preferably chosen from hydrochlorides, sulphates, hydrobromides and tartrates.

3-Methyl-para-aminophenol, 2-methyl-para-aminophenol and 2-hydroxymethyl-para-aminophenol, or their salts, are present at a total concentration of 0.01% to 4% by weight relative to the total weight of the dyeing composition, and preferably from 0.1 to 2% by weight.

The 2-methyl-5-aminophenols of formula (I) above, and their salts, represent in total from 0.005% to 5% by weight relative to the total weight of the dyeing composition, and preferably from 0.01 to 3.5% by weight.

Ortho-aminophenol or 3-acetylamino-6-aminophenol represent from 0.1% to 2% by weight relative to the total weight of the dyeing composition, and preferably from 0.2 to 1% by weight.

As a whole, the oxidation dye precursors and coupling agents according to the invention represent from 0.3 to 10% by weight, and preferably from 0.4 to 5% by weight, relative to the total weight of the composition.

The oxidizing agent is preferably chosen from hydrogen peroxide, urea peroxide, alkali metal bromates and persalts such as perborates and persulphates. Hydrogen peroxide is particularly preferred.

Composition (A), which contains the combination of dyes as described above, may have a pH between 3 and 10.5, which may be adjusted to the chosen value using basifying agents commonly used in the dyeing of keratinous fibres, such as aqueous ammonia, alkali metal carbonates, alkanolamines, for example mono-, di- and triethanolamines and their derivatives, sodium hydroxide or potassium hydroxide, the compounds of formula

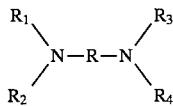

in which

R is a propylene residue which is optionally substituted with a hydroxyl group or a $C_1$–$C_4$ alkyl radical;

$R_1$, $R_2$, $R_3$ and $R_4$, simultaneously or independently of each other, represent a hydrogen atom, a $C_1$–$C_4$ alkyl or $C_1$–$C_4$ hydroxyalkyl radical; or standard acidifying agents such as inorganic or organic acids, for example hydrochloric, tartaric, citric and phosphoric acids.

The pH of composition (B) containing the oxidizing agent as defined above is such that, after mixing with composition (A), the pH of the composition applied to the human keratinous fibres preferably varies between 3 and 11. It is adjusted to the desired value using acidifying or optionally basifying agents which are well known in the state of the art, as described above.

The oxidizing composition (B) preferably consists of hydrogen peroxide solution.

According to a preferred embodiment of the dyeing process of the invention, the dyeing composition (A) described above is mixed at the time of use with an oxidizing solution in a sufficient amount to develop a coloration. The mixture obtained is subsequently applied to human keratinous fibres and is left to stand for 5 to 40 minutes, preferably 15 to 30 minutes, after which they are rinsed, washed with shampoo, rinsed again and dried.

According to the invention, the dyeing compositions may contain, in addition to the dyes defined above, other coupling agents and/or direct dyes, with a view in particular to tinting or enriching with glints the colours provided by the oxidation dye precursors.

These couplers are well known per se and are chosen from benzenic compounds bearing at least 2 substitutions in a meta position relative to each other and are different from the 2-methyl-5-aminophenols of formula (I) above, as well as their salts; α-naphthol; indole derivatives; coupling agents possessing an active methylene group, such as β-keto compounds; pyrazolones, and their salts.

The direct dyes are preferably azo or anthroquinone dyes or nitro derivatives of the benzenic series.

The dyeing compositions in accordance with the invention also contain, in their preferred embodiment, anionic, cationic, nonionic or amphoteric surface-active agents or their mixtures. Among these surface-active agents there may be mentioned alkylbenzenesulphonates, alkylnaphthalenesulphonates, sulphates, ether-sulphates and sulphonates of fatty alcohols. Alkyl polyglycosides, quaternary ammonium salts such as trimethylcetylammonium bromide, cetylpyridinium bromide, optionally oxyethylenated fatty acid ethanolamides, polyoxyethylenated acids, alcohols and amines, polyglycerolated fatty alcohols and polyoxyethylenated or polyglycerolated alkylphenols, as well as polyoxyethylenated alkyl sulphates.

These surface-active agents are present in the compositions in accordance with the invention in proportions between 0.5 and 55% by weight, and preferably between 2 and 50% by weight, relative to the total weight of the composition.

These compositions may also contain organic solvents in order to solubilize the components which would not be sufficiently soluble in water. Among these solvents there my be mentioned, as examples, $C_1$–$C_4$ lower alkanols such as ethanol and isopropanol; glycerol; glycols or glycol ethers such as 2-butoxyethanol, propylene glycol and the monoethyl ether and monomethyl ether of diethylene glycol, as well as aromatic alcohols such as benzyl alcohol or phenoxyethanol, analogous products and their mixtures.

The solvents are preferably present in proportions between 1 and 40% by weight, and in particular between 5 and 30% by weight, relative to the total weight of the composition.

The thickening agents which may be added to the compositions in accordance with the invention may be chosen from sodium alginate, gum arabic, optionally crosslinked acrylic acid polymers, cellulose derivatives and heterobiopolysaccharides such as xanthan gum; it is also possible to use inorganic thickening agents such as bentonite.

These thickening agents are preferably present in proportions between 0.1 and 5%, and in particular between 0.2 and 3% by weight, relative to the total weight of the composition.

The anti-oxidizing agents which may be present in the compositions are chosen in particular from sodium sulphite, thioglycolic acid, thiolactic acid, sodium bisulphite, dehydroascorbic acid, hydroquinone, 2-methylhydroquinone, tert-butylhydroquinone and homogentisic acid.

These anti-oxidizing agents are present in the composition in proportions between 0.05 and 1.5% by weight relative to the total weight of the composition.

These compositions may also contain other cosmetically acceptable adjuvants, for example such as penetration agents, sequestering agents, perfumes, buffers, dispersing agents, treatment agents, conditioning agents, film-forming agents, preserving agents and opacifying agents.

The composition applied to hair may be presented in diverse forms, such as in liquid, cream or gel form or in any other form which is suitable for dyeing keratinous fibres and in particular human hair. These compositions may be packaged under pressure in aerosol bottles in the presence of a propellent and may form foams.

The examples which follow are intended to illustrate the invention without, however, having a limiting nature.

EXAMPLE 1

The following dyeing composition is prepared:

| | |
|---|---|
| • Octyldodecanol sold under the name EUTANOL G by the company HENKEL | 8.0 g |
| • Oleic acid | 20.0 g |
| • Monoethanolamine lauryl ether sulphate sold under the name SIPON LM 35 by the company HENKEL | 3.0 g |
| • Ethyl alcohol | 10.0 g |
| • Benzyl alcohol | 10.0 g |
| • Cetyl/stearyl alcohol containing 33 moles of ethylene oxide sold under the name SIMULSOL GS by the company SEPPIC | 2.4 g |
| • Ethylenediaminetetraacetic acid | 0.2 g |
| • Aqueous solution at a concentration of 60% of AM of a cationic polymer consisting of the following repeating units: | 2.2 g AM |

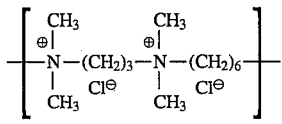

| | |
|---|---|
| • Monoethanolamine | 7.5 g |
| • Linoleic acid diethanolamide sold under the name COMPERLAN F by the company HENKEL | 8.0 g |
| • Aqueous ammonia containing of 20% of $NH_3$ | 10.2 g |
| • Sodium metabisulphite in aqueous solution at a concentration of 35% of AM | 0.46 g AM |
| • Hydroquinone | 0.15 g |
| • 1-Phenyl-3-methyl-5-pyrazolone | 0.2 g |
| • 3-Methyl-p-aminophenol | 0.9 g |
| • 2-Methyl-5-aminophenol | 1.2 g |
| • ortho-Aminophenol | 0.3 g |
| • Demineralized water qs | 100 g |

This composition is mixed weight for weight with 20 volumes hydrogen peroxide (6% by weight), of pH 3, at the time of use.

A mixture of pH 9.8 is obtained.

This mixture is applied to natural grey hair containing 90% white hair for 30 minutes. After rinsing, washing with shampoo, rinsing and drying, the hair is dyed a coppery golden colour.

EXAMPLES 2 TO 4

The following dyeing composition is prepared:

| | |
|---|---|
| • Polyglycerolated oleyl alcohol containing 2 moles of glycerol | 4.0 g |
| • Polyglycerolated oleyl alcohol containing 4 moles of glycerol (78% of AM) | 5.69 g AM |
| • Oleic acid | 3.0 g |
| • Oleyl amine containing 2 moles of ethylene oxide sold under the name ETHOMEEN O12 by the company AKZO | 7.0 g |
| • Diethylaminopropyl laurylaminosuccinamate, sodium salt containing 55% of AM | 3.0 g AM |
| • Oleyl alcohol | 5.0 g |
| • Oleic acid diethanolamide | 12.0 g |
| • Propylene glycol | 3.5 g |
| • Ethyl alcohol | 7.0 g |
| • Dipropylene glycol | 0.5 g |
| • Propylene glycol monomethyl ether | 9.0 g |
| • Sodium metabisulphite in aqueous solution containing 35% of AM | 0.455 g AM |
| • Ammonium acetate | 0.8 g |
| • Anti-oxidizing agent, sequestering agent qs | |
| • Perfume, preserving agent qs | |
| • Aqueous ammonia containing 20% of $NH_3$ | 10.0 g |
| • Dyes | x g |
| • Demineralized water qs | 100 g |

This composition is mixed weight for weight with 20 volumes hydrogen peroxide (6% by weight), of pH 3, at the time of use.

A mixture of pH indicated in the table below is obtained.

This mixture is applied to grey hair containing 90% white, natural or permanent-waved hair, for 30 minutes. After rinsing, washing with shampoo, rinsing and drying, the hair is dyed in the shades indicated in the table below.

TABLE

| | Example | | | |
|---|---|---|---|---|
| | 2 | 3 | 4 | 5 |
| 3-Methyl-p-aminophenol | 1.5 g | 1.0 g | | 1.0 g |
| 2-Methyl-p-aminophenol | | | 0.5 g | |
| 2-Hydroxyethyl-p-aminophenol | | | 0.5 g | |
| 2-Methyl-5-aminophenol | 2.0 g | 1.3 g | | |
| 2-Methyl-5-N-(β-hydroxyethyl)-aiminophenol | | | 1.3 g | |
| 2-Methyl-5-N-methyl-aminophenol | | | | 0.5 g |
| 2-Methyl-5-N-ethyl-aminophenol | | | | 0.5 g |
| ortho-Aminophenol | 0.7 g | | 0.5 g | 0.5 g |
| 3-Acetylamino-6-aminophenol hydrochloride | | 0.5 g | | |
| pH of the mixture | 9.6 | 9.6 | 9.6 | 9.6 |
| SHADE OBTAINED: | | | | |
| on natural grey hair containing 90% white hair | | Coppery iridescent | | Coppery golden |
| on permanent-waved grey hair containing 90% white hair | Intense coppery red dark blond | light blond | Coppery golden blond | |

We claim:

1. Dyeing composition for keratinous fibres, comprising, in a suitable dyeing medium:

an effective amount for dyeing said keratinous fibres of at least one oxidation dye precursor selected from the group consisting of 3-methyl-para-aminophenol, 2-methyl-para-aminophenol, 2-hydroxymethyl-para-aminophenol and their acid addition salts;

an effective amount for dyeing said keratinous fibres of at least one coupling agent selected from the group consisting of 2-methyl-5-aminophenols of formula (I) below:

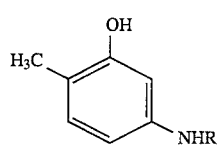

in which R denotes a hydrogen atom, a methyl or ethyl radical or a β-hydroxyethyl or γ-hydroxypropyl group, and their acid addition salts; and an effective amount for dyeing said keratinous fibres of at least one ortho-aminophenol, as oxidation dye precursor, selected from the group consisting of ortho-aminophenol, 3-acetylamino-6-aminophenol, and their acid addition salts.

2. Dyeing composition according to claim 1, wherein the para-aminophenol oxidation dye precursor is 3-methyl-para-aminophenol or one of its acid addition salts.

3. Dyeing composition according to claim 1, wherein the coupling agent is 2-methyl-5-aminophenol or one of its acid addition salts.

4. Dyeing composition according to claim 1, wherein the acid addition salts are selected from the group consisting of hydrochlorides, sulphates, hydrobromides and tartrates.

5. Dyeing composition according to claim 1, which contains a total concentration of 0.01% to 4% by weight relative to the total weight of the composition of at least one oxidation dye precursor selected from the group consisting of 3-methyl-para-aminophenol, 2-methyl-para-aminophenol, 2-hydroxymethyl para-aminophenol, and their acid addition salts.

6. Dyeing composition according to claim 1, wherein the 2-methyl-5-aminophenols of formula (I) or their salts are present at a total concentration of 0.005 to 5% by weight relative to the total weight of the composition.

7. Dyeing composition according to claim 1, which contains a total concentration of 0.1 to 2% by weight relative to the total weight of the composition of at least one ortho-aminophenol selected from the group consisting of ortho-aminophenol, 3-acetylamino-6-aminophenol and their acid addition salts.

8. Dyeing composition according to claim 1, wherein the oxidation dye precursors and the coupling agents are present in a total concentration of 0.3 to 10% by weight relative to the total weight of the composition.

9. Dyeing composition according to claim 1, which has a pH between 3 and 10.5.

10. Dyeing composition according to claim 1, which contains other coupling agents selected from the group consisting of α-naphthol, indole derivatives, β-keto compounds, pyrazolones, and their salts.

11. Dyeing composition according to claim 1, which additionally contains direct dyes selected from the group consisting of azo and anthraquinone dyes and nitro derivatives of the benzenic series.

12. Dyeing composition according to claim 1, which additionally contains at least one adjuvant selected from the group consisting of anionic, cationic, nonionic and amphoteric surface-active agents and their mixtures in proportions between 0.5 and 55% by weight, organic solvents in proportions between 1 and 40% by weight, thickening agents in proportions between 0.1 and 5% by weight and anti-oxidizing agents in proportions between 0.05 and 1.5% by weight, the proportions being calculated relative to the total weight of the composition, penetration agents, sequestering agents, perfumes, buffers, dispersing agents, conditioning agents, film-forming agents, preserving agents and opacifying agents.

13. Composition for the dyeing of keratinous fibres, according to claim 1, which composition additionally contains an oxidizing agent and has a pH between 3 and 11.

14. Composition according to claim 13, wherein the oxidizing agent is a hydrogen peroxide solution.

15. Agent for the dyeing of keratinous fibres, comprising at least two components: a component (A) consisting of a dyeing composition according to any claim 1 and a component (B) comprising an oxidizing agent in a suitable dyeing medium.

16. Dyeing agent according to claim 15, wherein the oxidizing agent is selected from the group consisting of hydrogen peroxide, urea peroxide, alkali metal bromates, perborates and persulphates.

17. Process for the dyeing of keratinous fibres, comprising applying to the fibres a dyeing composition according to claim 1, and developing a colour in an acidic or alkaline medium by means of an oxidizing agent added at the time of applying this composition or present in a second composition applied simultaneously or sequentially.

18. Dyeing process according to claim 17, wherein the dyeing composition is mixed at the time of applying to the fibers with an oxidizing solution in a sufficient amount to develop a coloration, the mixture obtained is then applied to the fibres, it is left to stand for 5 to 40 minutes, and is then rinsed, washed with shampoo, rinsed again and dried.

19. Device or dyeing kit containing at least two compartments, a first compartment of which contains the composition as defined in claim 1, and a second compartment of which contains a composition comprising an oxidizing agent in a suitable dyeing medium.

20. Dyeing composition according to claim 5, wherein the oxidation dye precursor is present in a total concentration of 0.1 to 2% by weight.

21. Dyeing composition according to claim 6, wherein the 2-methyl-5-aminophenols of formula (I) or their salts are present at a total concentration of 0.01 to 3.5% by weight.

22. Dyeing composition according to claim 7, wherein the ortho-aminophenol is present at a total concentration of 0.2 to 1% by weight.

23. Dyeing composition according to claim 8, wherein the oxidation dye precursors and the coupling agents are present in a total concentration of 0.4 to 5% by weight.

* * * * *